United States Patent
Yamamoto et al.

(10) Patent No.: US 7,526,948 B2
(45) Date of Patent: May 5, 2009

(54) DEVICE AND METHOD FOR DETECTING FOREIGN MATERIAL ON THE SURFACE OF PLASMA PROCESSING APPARATUS

(75) Inventors: Hideyuki Yamamoto, Kudamatsu (JP); Hiromichi Enami, Kudamatsu (JP); Muneo Furuse, Kudamatsu (JP)

(73) Assignee: Hitachi High-Technologies Corporation, Tokyo (JP)

( * ) Notice: Subject to any disclaimer, the term of this patent is extended or adjusted under 35 U.S.C. 154(b) by 472 days.

(21) Appl. No.: 11/214,963

(22) Filed: Aug. 31, 2005

(65) Prior Publication Data
US 2007/0032088 A1   Feb. 8, 2007

(30) Foreign Application Priority Data
Aug. 5, 2005   (JP) ............................... 2005-227887

(51) Int. Cl.
  *G01N 1/08*   (2006.01)
  *G01M 19/00*  (2006.01)
  *H01L 21/66*  (2006.01)
(52) U.S. Cl. ........................... 73/104; 73/864.33; 73/37
(58) Field of Classification Search ................... 73/104, 73/865.9, 37, 863.21, 864.33
  See application file for complete search history.

(56) References Cited

U.S. PATENT DOCUMENTS

| 4,661,203 | A | | 4/1987 | Smith |
| 5,607,515 | A | * | 3/1997 | Takahashi .................... 134/18 |
| 5,939,647 | A | * | 8/1999 | Chinn et al. .......... 73/864.33 X |
| 5,942,699 | A | * | 8/1999 | Ornath et al. ............. 73/863.21 |
| 6,327,021 | B1 | * | 12/2001 | Higashiguchi ................ 355/30 |
| 6,408,701 | B1 | * | 6/2002 | Fujita .................. 73/864.33 X |
| 6,755,934 | B2 | * | 6/2004 | Matsuoka .............. 156/345.33 |
| 6,848,325 | B2 | * | 2/2005 | Parmeter et al. ......... 73/864.33 |
| 2007/0023065 | A1 | * | 2/2007 | Kim et al. ..................... 134/1.2 |

FOREIGN PATENT DOCUMENTS

| JP | 7-103863 | | 4/1995 |
| JP | 11083694 | A * | 3/1999 |
| JP | 2000-321180 | | 11/2000 |
| JP | 2001250802 | A * | 9/2001 |

* cited by examiner

*Primary Examiner*—Thomas P Noland
(74) *Attorney, Agent, or Firm*—Antonelli, Terry, Stout & Kraus, LLP.

(57) ABSTRACT

A detection technique for detecting foreign material on the surface of a plasma processing apparatus, capable of accurately sucking/extracting and measuring foreign material contained in the measurement object surface is provided. The detection device comprises a gauge head or probe having a gas blow out opening for intermittently blowing a gas of a predetermined pressure to a measurement object surface and a gas suction opening for sucking foreign material discharged by the gas blown out from the gas blow out opening a particle counter having a suction pump for continuously sucking in a predetermined amount of gas from the gas suction opening for counting the number of foreign material particles contained in the gas sucked by the suction pump and a pressure adjustment unit for intermittently supplying gas of a predetermined pressure to the gas blowing out opening.

13 Claims, 2 Drawing Sheets

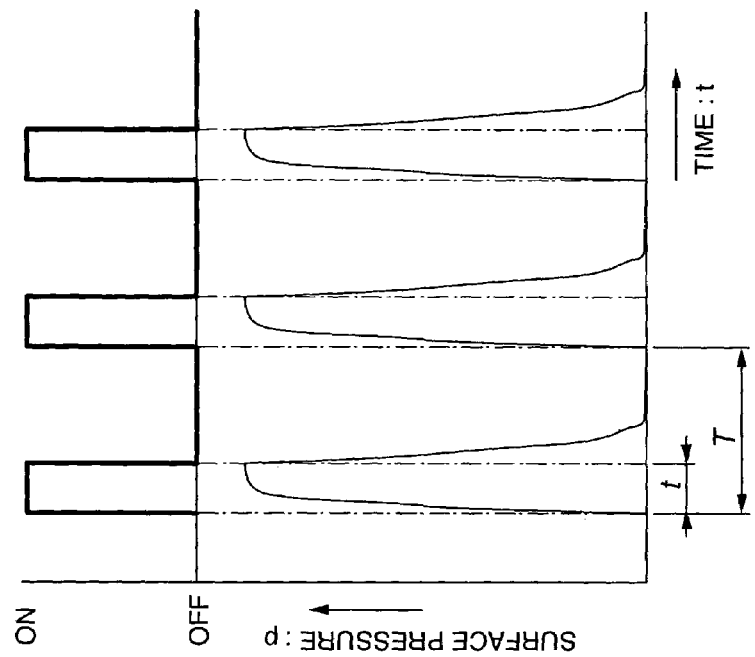
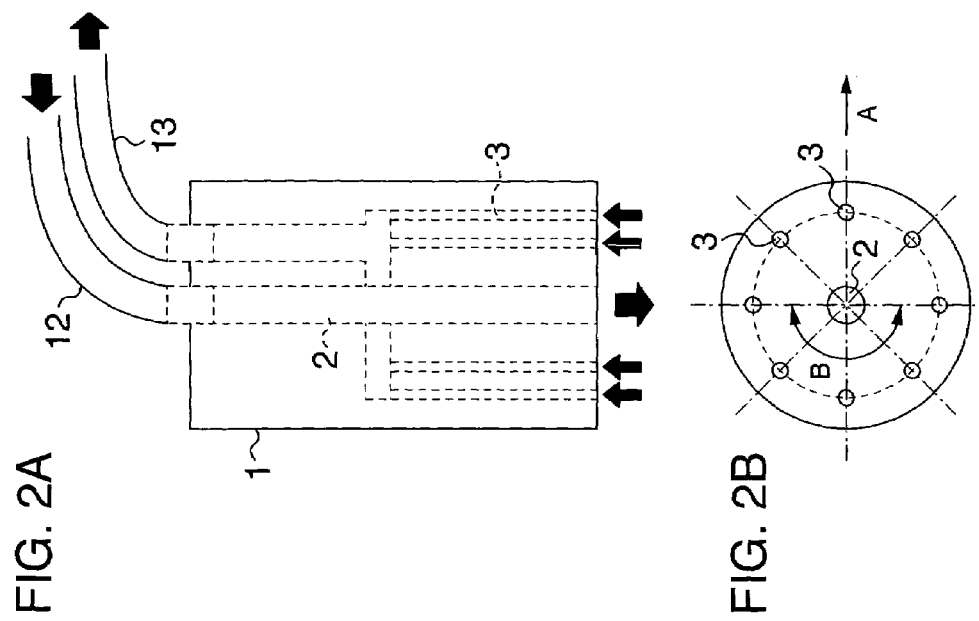

DEVICE AND METHOD FOR DETECTING FOREIGN MATERIAL ON THE SURFACE OF PLASMA PROCESSING APPARATUS

INCORPORATION BY REFERENCE

The present application claims priority from Japanese application JP2005-227887 filed on Aug. 5, 2005, the content of which is hereby incorporated by reference into this application.

BACKGROUND OF THE INVENTION

The present invention relates to a technique for detecting foreign material on the surface of plasma processing apparatus, i.e., for detecting foreign material accumulated on the surface of the processing chamber of the plasma processing apparatus.

The surface of various parts used in the vacuum processing chamber of the plasma processing apparatus is processed by the anode oxidization method such as metal oxide or ceramics, alumite processing or polishing processing. However, according to the washing state after the processing, the washing state after the wet cleaning, or the change of the surface state by the plasma processing, minute foreign material (particles) may be emitted into the processing chamber during operation of the device. The foreign material adheres to the surface of the sample to be processed, causing processing defect of a semiconductor device as a product and lowering the yield or the device operation efficiency.

For this, for example, when reassembling the vacuum processing chamber after the wet cleaning, it is necessary to accurately manage the amount of the foreign material adhering to surface of the respective parts constituting the vacuum processing chamber.

As a device for measuring the foreign material, JP-A-2000-321180 discloses a surface contamination measuring device including suction means for sucking in the air from the vicinity of the measuring object, a measuring unit for measuring the amount and component of the particles in the sucked air, and discharge means for discharging a fluid to the surface of the measuring object. Moreover, this measuring device includes a shielding member formed by a flexible member around the sampling member forming an air suction hole and discharge hole, thereby effectively catching particles.

Moreover, JP-A-7-103863 discloses a device including a spray nozzle for spraying gas to the surface of the measurement object parts, a catch suction tube for collecting the gas sprayed to the surface of the parts via the spray nozzle, and inspection means such as a dust counter for inspecting the adhering material contained in the gas sent into the catch suction tube.

SUMMARY OF THE INVENTION

According to the technique disclosed in JP-A-2000-321180, the clearance between the measuring object surface and the sampling member is filled with a flexible member and it is possible to effectively detect particles. However, since the flexible member is brought into contact with the measurement object member, contamination may be caused. Moreover, the inner pressure of the space sealed by the flexible member increases or decreases. In this case, a measurement error is easily caused.

Moreover, according to the technique of JP-A-7-103863, gas is sprayed to the part surface via a nozzle and the gas sprayed is collected so as to evaluate the part surface. However, no consideration is taken for processing for scattering of particles by the gas sprayed.

Moreover, the gas blow out means disclosed in JP-A-2000-321180 and the spray nozzle disclosed in JP-A-7-103863 continuously supply the gas for measurement to the measurement object surface. For this, the scattering amount of the foreign material is increased and the contamination range in the processing chamber is enlarged. Moreover, in the measurement device disclosed in JP-A-2000-321180, a measurement error is caused by the fluctuation of the inner pressure of the space sealed as has been described above. That is, it is difficult to accurately predict the generation state of foreign material when the vacuum processing chamber is actually used.

It is therefore an object of the present invention to provide a technique for detecting foreign material on the surface of the plasma processing apparatus capable of accurately suction-extracting and measuring the foreign material contained on the surface of the measurement object.

In order to achieve the aforementioned object, the present invention employs the measures as follows.

The device includes: a gauge head having a gas blow out opening for intermittently blowing out gas of a predetermined pressure onto a measurement object surface and a gas suction opening for sucking in the foreign material emitted by the gas blown from the gas blow out opening; a suction pump for continuously sucking in a constant amount of gas from the gas suction opening; a particle counter for counting the foreign particles contained in the gas sucked in by the suction pump; and a pressure adjustment unit for intermittently supplying gas of a predetermined pressure to the gas blow out opening.

Other objects, features and advantages of the invention will become apparent from the following description of the embodiments of the invention taken in conjunction with the accompanying drawings.

BRIEF DESCRIPTION OF THE DRAWINGS

FIGS. 2A, 2B, 2C explain details of the gauge head.

DESCRIPTION OF THE EMBODIMENTS

Figure 1A:
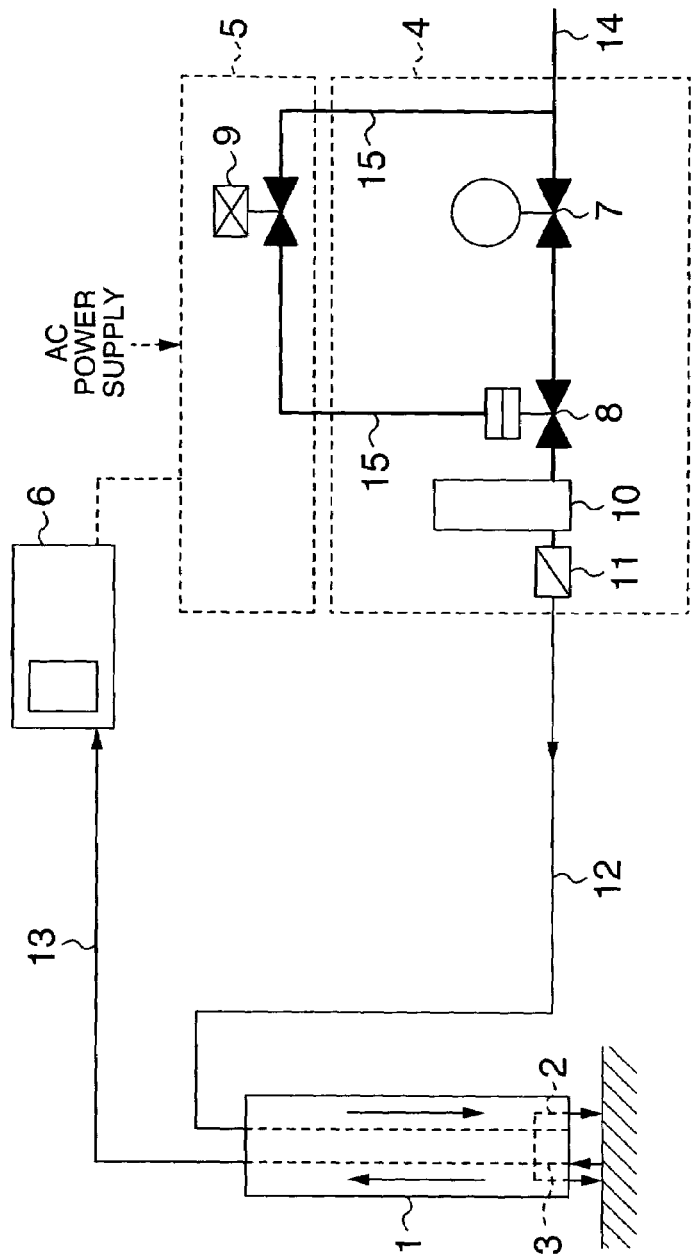
FIGS. 1A and 1B explain the device for detecting foreign material on the surface of the plasma processing apparatus according to an embodiment of the present invention.
Figure 1B:
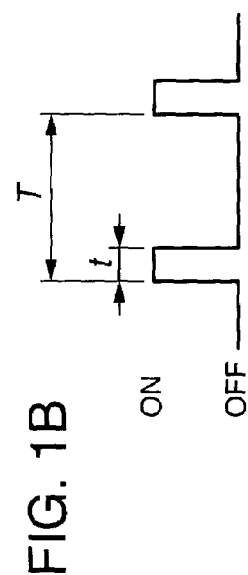

Description will now be directed to an embodiment of the present invention with reference to the attached drawings. FIG. 1 explains the device for detecting foreign material on the surface of a plasma processing apparatus according to the embodiment of the present invention. FIG. 1A shows the entire device. FIG. 1B explains the gas supply timing.

In FIG. 1A, the reference numeral 1 denotes a gauge head (probe) and 2 denotes a blow out opening. It is possible to intermittently blow a gas (for example, air) of a predetermined pressure to a measurement object surface. The reference numeral 3 denotes a suction opening for sucking in the foreign material emitted by the gas blow out from the blow out opening. The reference numeral 4 is a pressure adjustment unit for adjusting the gas obtained from an air steel bottle or the like to a predetermined pressure and intermittently supplying the gas of the adjusted pressure to the blow out opening 2.

The reference numeral 5 is a control unit and 6 is a particle counter. The particle counter 6 has a suction pump and counts the number of foreign particles contained in the gas sucked in by the suction pump. The particle counter can detect a minute particle of the order of 0.1 μm. Thus, it is possible to judge the cleaning degree of the part surface.

The reference numeral 14 is a connection pipe to the gas steel bottle. The reference symbol 7 is a pressure adjustment vessel for adjusting the pressure of the gas steel bottle (0.55 Mp) to a constant pressure p (for example 0.1 Mp or 0.5 Mp) and intermittently supplying the gas of the adjusted pressure to the blow out opening 2. The reference numeral 8 denotes an air drive valve, and 9 denotes an electromagnetic valve for driving the air drive valve 8. According to a control signal from the control unit 5, the electromagnetic valve 9 supplies the gas of the comparatively high pressure from the gas steel bottle via the pipe 15 to the air drive valve 8 so as to open/close the air drive valve 8. Thus, it is possible to supply the gas adjusted to a constant pressure p to the blow out opening 2.

The reference numeral 10 denotes an ionizer for ionizing the gas supplied to the blow out opening. The reference numeral 11 denotes an in-line filter for removing in advance minute foreign particles (0.001 μm or below) contained in the gas supplied. The reference numeral 12 denotes a flexible pipe connecting the pressure adjustment unit 4 to the gauge head 1. The reference numeral 13 is a flexible pipe connecting the gauge head 1 to the particle counter. The pipes 12 and 13 can be formed as a unitary block.

FIG. 1B explains the supply timing of the gas to be supplied to the gas blow out opening. As shown in the figure, it is preferable that the gas supply time t for supplying the gas to the gas blow out opening be set to less than 1 second and the gas supply cycle T be adjusted in a range from 2 to 6 seconds.

Thus, in this embodiment, the compressed gas is intermittently blown to the measurement object subject from the blow out opening 2. Thus, the foreign material firmly adhering to the measurement object surface can be surely peeled off by the shot-time shock by the blown gas. Moreover, the foreign material peeled off is caught by the gas flow sucked at a constant speed by the suction pump arranged in the particle counter and conveyed to the particle counter for counting the number of foreign particles coming from the gas suction opening.

Moreover, it is possible to arbitrarily determine the pressure p, the blow out time t and the blow out cycle T of the gas blow out from the blow out opening. Accordingly, as compared to the method for blowing out the gas constantly from the gas blow opening, the foreign particles can be easily peeled off the surface and it is possible to accurately measure the amount of the foreign material contained in the measurement object surface. That is, it is possible to know the foreign material generation state which is near to the actual use state of the vacuum processing chamber (almost all the foreign particles are discharged).

It should be noted that as has been described above, the measurement object surface has been subjected to a surface processing such as alumite layer. The surface processing layer formed on the surface normally includes a number of crystalline grain boundaries and has a small expansion ratio as compared to the aluminum as an undercoat layer. For this, by heating the measurement object including the alumite layer, it is possible to promote discharge of the foreign material adhering to the surface. Accordingly, when performing measurement by the gauge head, it is advantageous to heat the measurement object by a heating device (bake heater).

Moreover, as has been described above, it is possible to arrange an ionizer in the gas supply path for supplying gas to the gas blow out opening and ionizing the gas to be supplied. In this case, the ionized gas neutralizes the electric charge of the foreign material adhering to the measurement object surface and promotes discharge of the foreign material.

FIG. 2 explains the detailed of the gauge head. FIG. 2A is a side view of the gauge head, FIG. 2B is a bottom view of the gauge head, and FIG. 2C shows the pressure of the gas blown to the measurement object surface. As shown in the figures, the gauge head 1 has a cylindrical shape and the blow out opening 2 is arranged at the center of the bottom (surface opening to the measurement object surface) of the cylindrical gauge head 1. A plurality of suction openings 3 are arranged around the blow out opening 2.

It should be noted that it is possible to arrange the blow out opening 2 at a plurality of positions. Moreover, the suction opening may be formed as a continuous groove communicating to the suction openings arranged around the blow out opening 2. Moreover, when performing measurement while scanning the gauge head 1 on the measurement object surface, there is no need of using the gauge head of the type in which the blow out opening 2 is entirely surrounded by the suction openings 3. In this case, the gas blow out opening 2 is arranged at the front direction (in the direction A in the figure) of the scan direction of the surface opposing to the measurement object surface of the gauge head while the gas suction opening is arranged only at the rear direction of the scan direction (in the range of arrow B) of the surface opposing to the measurement object surface of the gauge head.

Moreover, the pressure of the gas blown to the measurement object surface is suddenly changes as shown in FIG. 2C. For this, it is possible to suck/extract almost all of the foreign particles contained in the measurement object surface and count them.

As has been described above, according to the present embodiment, by using the gauge head having the gas blow out opening and the gas suction opening for sucking in the foreign material discharged by the blown out gas from the gas blow out opening, it is possible to intermittently to blow the compressed gas and apply a shock to the measurement object surface to promote emission of the foreign material while suppressing scattering of the foreign material adhering to the measurement object. Moreover, by using the gauge head in which the blow out opening and the suction opening are formed in a unitary block, the intermittently blown gas is continuously sucked at a constant speed from the gas suction opening. Accordingly, it is possible to perform detection of foreign material having a preferable repeatability not depending on the measurement place or the measurement operator.

With the aforementioned configuration, the present invention can provide a technique for detecting foreign material on the surface of the plasma processing apparatus capable of accurately sucking/extracting foreign material contained in the measurement object surface.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A detection method for detecting a foreign material on a surface of a plasma processing apparatus, the method comprising steps of:

using a gauge head having a gas blow out opening, arranged at a central portion of a surface of the gauge head, for intermittently blowing a gas of a predetermined pressure from the gas blow out opening to a measurement portion of the surface of the plasma processing apparatus, and a gas suction opening, arranged outside of the central portion of the surface of the gauge head, for sucking the foreign material discharged by the gas blown out from the gas blow out opening;

intermittently supplying gas of a predetermined pressure through the gas blow out opening to the measurement portion of the surface opposing the gauge head; and sucking a predetermined amount of gas through the gas suction opening from a proximity of the measurement portion of the surface of the plasma processing apparatus, and counting the number of foreign material particles contained in the sucked amount of gas.

2. A detection method according to claim 1, wherein a time for the intermittent supply of the gas through the gas blow out opening is preset to less than one second, and the gas supply cycle is preset to 2 to 6 seconds.

3. A detection method according to claim 1, further comprising a step of ionizing a supply gas in a gas supply path for supplying the gas to the gas blow out opening.

4. A detection method according to claim 1, further comprising a step of heating the measurement portion of the surface of the plasma processing apparatus during the detection of the foreign material.

5. A detection method according to claim 1, wherein the foreign material on the surface of the plasma processing apparatus is a residue resulting from a maintenance cleaning procedure performed after plasma processing by the plasma processing apparatus.

6. A detection method according to claim 1, wherein the method for detecting the foreign particles is performed during reassembling of the plasma processing apparatus after performing a wet cleaning of the plasma processing apparatus procedure.

7. A detection method for detecting a foreign material on a surface of a plasma processing apparatus, the method comprising the steps of:

using a gauge head having a gas blow out opening for blowing a gas of a predetermined pressure to a measurement surface of the plasma processing apparatus and a gas suction opening for sucking foreign material discharged from the measurements surface by the gas blown out from the gas blow out opening;

moving a front portion of the gauge head in a predetermined scanning direction on the measurement surface;

intermittently supplying gas of a predetermined pressure through the gas blow out opening to the measurement; and sucking a predetermined amount of gas through the gas suction opening, and counting the number of foreign material particles contained in the sucked gas;

wherein the gas blow out opening is arranged on the front portion of the gauge head surface opposing the measurement surface relative to the gas suction opening with regard to the predetermined scanning direction.

8. A detection method for detecting a foreign material on an object on a surface of a plasma processing apparatus, the method comprising steps of:

using a gauge head having a gas blow out opening, arranged at the center of the surface of the gauge head opposing the object surface, for blowing a gas of a predetermined pressure to the measurement object surface, and a plurality of gas suction openings, arranged in a pattern radially outward from the blow out opening, for sucking foreign material discharged by the gas blown out from the gas blow out opening;

placing the gauge head in a close proximity to the object surface;

intermittently supplying the gas of a predetermined pressure from the gas blow out opening to the object surface opposing to the gauge; and continuously sucking a predetermined amounts of gas from the gas suction opening, and counting the number of the foreign material particles contained in the sucked gas.

9. A detection method according to claim 8, wherein a time for the intermittent supply of the gas through the gas blow out opening is preset to less than one second, and the gas supply cycle is preset to 2 to 6 seconds.

10. A detection method according to claim 8, further comprising a step of ionizing a supply gas in a gas supply path for supplying the gas to the gas blow out opening.

11. A detection method according to claim 8, further comprising a step of heating the object surface during the detection of the foreign material.

12. A detection method according to claim 8, wherein the foreign material on the object on the surface of the plasma processing apparatus is a residue resulting from a maintenance cleaning procedure performed after plasma processing by the plasma processing apparatus.

13. A detection method according to claim 8, wherein the method for detecting the foreign particles is performed during reassembling of the plasma processing apparatus after a wet cleaning procedure of the plasma processing apparatus.

\* \* \* \* \*